United States Patent [19]

Nakazawa et al.

[11] Patent Number: 5,492,818
[45] Date of Patent: Feb. 20, 1996

[54] METHOD OF PRODUCING L-GLUTAMIC ACID BY FERMENTATION

[75] Inventors: Hidetsugu Nakazawa; Hiroki Kawashima; Inao Oyama; Keiji Ishii; Yoshio Kawahara, all of Kawasaki, Japan

[73] Assignee: Ajinomoto Co., Inc., Tokyo, Japan

[21] Appl. No.: 354,014

[22] Filed: Dec. 5, 1994

Related U.S. Application Data

[63] Continuation of Ser. No. 114,843, Sep. 2, 1993, abandoned.

[30] Foreign Application Priority Data

Feb. 16, 1993 [JP] Japan ..................... 5-026811

[51] Int. Cl.⁶ ............................. C12P 13/14; C12P 13/18
[52] U.S. Cl. .......................... 435/111; 435/106; 435/110; 435/252.32; 435/843
[58] Field of Search ..................... 435/106, 110, 435/111, 843, 252.32

[56] References Cited

U.S. PATENT DOCUMENTS 4,411,991  10/1983  Hirakawa et al. ..................... 435/843

OTHER PUBLICATIONS

Liebl et al., *International Journal of Systematic Bacteriology*, vol. 41, pp. 255–260 (1991).
Agric. Biol. Chem., vol. 44, No. 8, (1980), pp. 1897–1904, Isamu Shiio et al, "Presence and Regulation of α-Ketoglutarate . . . in a Glutamate–Producing Bacterium, *Brevibacterium flavum*".
Agric. Biol. Chem., vol. 46, No. 2, (1982), pp. 493–500, Isamu Shiio et al, "Glutamate Metabolism in a Glutamate–producing Bacterium, *Brevibacterium flavum*".

*Primary Examiner*—Herbert J. Lilling
*Attorney, Agent, or Firm*—Oblon, Spivak, McClelland, Maier, & Neustadt

[57] ABSTRACT

The present invention provides a method of producing L-glutamic acid by fermentation, comprising the steps of culturing a mutant of an L-glutamic acid-producing microorganism of the genus *Brevibacterium* or *Corynebacterium* which has lower α-ketoglutaric acid dehydrogenase activity compared with the wild strains from which said mutant is derived, in a liquid nutrient culture medium containing biotin at a concentration of 10 to 1000 µg/l without adding a biotin activity-suppressing substance thereto;

producing and accumulating L-glutamic acid in the culture solution; and recovering L-glutamic acid from said culture solution.

According to the method of the present invention, it is possible to industrially produce L-glutamic acid by fermentation in a more economical and efficient manner.

7 Claims, No Drawings

METHOD OF PRODUCING L-GLUTAMIC ACID BY FERMENTATION

This application is a continuation of application Ser. No. 08/114,843, filed on Sep. 2, 1993, now abandoned.

FIELD OF THE INVENTION

The present invention relates to a method of producing L-glutamic acid by fermentation. L-Glutamic acid is an important amino acid in foods, medicines, chemicals, etc.

DESCRIPTION OF THE PRIOR ART

Microorganisms belonging to the genus *Brevibacterium* or *Corynebacterium* are known to produce L-glutamic acid. A mutant strain of a L-glutamic acid-producing microorganism of the genus *Brevibacterium* has also been reported. The α-ketoglutaric acid dehydrogenase activity of the mutant was shown to be lower than that of its parent strain; however, the productivity of L-glutamic acid by the mutant was demonstrated to be similar to the productivity of the parent strain (*Agric. Biol. Chem.* (1980) 44: 1897–1904; *Agric. Biol. Chem.* (1982) 46: 493–500).

L-glutamic acid is industrially produced by fermentation using microorganisms belonging to the genus *Brevibacterium* or *Corynebacterium*. Various methods of culturing these microorganisms have been employed in order to maximize the productivity of L-glutamic acid. For example, it is known that biotin is an essential factor for the growth of these microorganisms and that the concentration of biotin or a biotin-active substance in the culture medium greatly influences the excretion of L-glutamic acid by these microorganisms. When these microorganisms are cultivated in media containing restricted amounts of biotin or a biotin-active substance required for the growth of the microorganisms, the production of L-glutamic acid increases. However, the common carbon source used in culture media is inexpensive material such as cane molasses or beet molasses which contains too much biotin to give high yields of L-glutamic acid. Accordingly, a penicillin such as penicillin G, F, K, O, V, X, etc., or a surfactant composed of a higher fatty acid or a derivative thereof such as sucrose monopalmitate, polyoxyethylene sorbitan monopalmitate, etc., must be added to the medium to suppress the biotin activity at the early logarithmic growth phase of the microbial cells. It is highly desirable to find a method for the industrial production of L-glutamic acid which is not influenced by the amount of biotin in the culture media.

SUMMARY OF THE INVENTION

Accordingly, one object of the present invention is to provide an improved method for the industrial production of L-glutamic acid by fermentation which is more economical and more efficient than previously known methods.

DETAIL DESCRIPTION OF THE PREFERRED EMBODIMENTS

The present inventors have now discovered that, when a mutant of a L-glutamic acid-producing microorganism of the genus *Brevibacterium* or *Corynebacterium*, which has lower α-ketoglutaric acid dehydrogenase activity compared with the wild strain from which said mutant is derived, is cultured in a liquid nutrient medium containing an excess amount of biotin, L-glutamic acid is produced at a high accumulation and at a high yield without the necessity of adding to the medium a biotin activity-suppressing substance.

Thus, the present invention provides a method of producing L-glutamic acid by fermentation, comprising culturing a mutant of a L-glutamic acid-producing microorganism of the genus *Brevibacterium* or *Corynebacterium*, wherein said mutant has a lower α-ketoglutaric acid dehydrogenase activity compared with the wild strain from which said mutant is derived, in a liquid nutrient medium containing biotin at a concentration of from 10 to 1000 µg/l without adding a biotin activity-suppressing substance thereto; producing and accumulating L-glutamic acid in the culture solution; and recovering L-glutamic acid from said culture solution.

Suitable mutants useful in accordance with the present invention may be any mutant which is induced from a L-glutamic acid producing microorganism of the genus *Brevibacterium* or *Corynebacterium* and which has a lower α-ketoglutaric acid dehydrogenase activity compared with the wild strain from which it is derived. The mutant may also have other characteristics which enhance the productivity of L-glutamic acid including resistance to compounds having vitamin-P activity, resistance to Decoyinine or Tubercidin, increased superoxide dismutase activity, as well as other such characteristics as described in U.S. Pat. Nos. 4,334,020, 4,389,483 and 4,529,697, incorporated herein by reference.

The following mutant strains may be used:

*Brevibacterium lactofermentum* (*Corynebacterium glutamicum*) AJ 12821 (FERM BP-4172);

*Brevibacterium flavum* (*Corynebacterium glutamicum*) AJ 12822 (FERM BP-4173) and

*Corynebacterium glutamicum* AJ 12823 (FERM BP-4174).

These mutants can be obtained by artificially mutating L-glutamic acid-producing strains belonging to the genus *Brevibacterium* or *Corynebacterium*. The parent strain is not particularly limited so long as it belongs to the genus *Brevibacterium* or *Corynebacterium* and is capable of producing L-glutamic acid. The following wild strains may be used:

*Brevibacterium lactofermentum* (*Corynebacterium glutamicum*) ATCC 13869;

*Brevibacterium flavum* (*Corynebacterium glutamicum*) ATCC 14067;

*Brevibacterium divaricatum* (*Corynebacterium glutamicum*) ATCC 14020;

*Brevibacterium roseum* ATCC 13825;

*Brevibacterium saccharolyticum* ATCC 14066;

*Corynebacterium glutamicum* ATCC 13032;

*Corynebacterium acetoacidophilum* ATCC 13870;

*Corynebacterium acetoglutamicum* ATCC 15806;

*Corynebacterium lilium* (*Corynebacterium glutamicum*) ATCC 15990 and

*Corynebacterium melassecola* ATCC 17965.

The mutants according to the present invention may be obtained by mutating wild type strains according to conventional techniques such as ultraviolet irradiation, X-ray irradiation, radioactive irradiation or treatment with a mutagenic agent. Typically, the mutants are obtained by mutating wild type strains with 250 µg/ml of N-methyl-N'-nitro-N-nitrosoguanidine at 30° C. for 20 minutes. Mutants may alternatively be obtained by recombinant DNA technique.

Suitable methods for isolating the mutants according to the present invention from the wild type cells after mutagenesis are not particularly limited and include, for example, a method of isolating strains which cannot grow on a medium containing L-glutamic acid as the only carbon and nitrogen source, but are capable of growing on a medium in which the L-glutamic acid in the above-stated medium has been substituted with succinic acid and ammonia (see *Agric. Biol. Chem.*(1982) 46: 493–500, incorporated herein by reference).

Mutants useful in accordance with the present invention have α-ketoglutaric acid dehydrogenase activities which are lower than the wild strains from which they are derived. The degree to which their activities are lowered is not necessarily limited, but it is preferable to use a mutant whose activity is between 1/5 and 1/500 of that of the parent strain, and more preferably between 1/10 and 1/100 thereof.

In order to produce and accumulate L-glutamic acid using the obtained mutant, the cultivation is effected in a liquid nutrient medium wherein a material containing an excess amount of biotin, such as cane molasses or beet molasses, is used as the carbon source. Alternatively, a liquid medium in which biotin is added in an excess amount to a carbon source, such as a saccharified solution or acetic acid may be used.

Conventionally, when the cultivation is effected in a liquid medium containing an excess amount of biotin, it has been necessary to add a substance thereto to suppress the biotin activity such as a penicillin such as penicillin G, F, K, O, V or X or a surfactant composed of a higher fatty acid or a derivative thereof such as sucrose monopalmitate or polyoxyethylene sorbitan monopalmitate in order to produce L-glutamic acid at a high yield. However, if a mutant according to the present invention is used which has a lower α-ketoglutaric acid dehydrogenase activity than the wild strain from which it is derived, then L-glutamic acid may be produced and accumulated at a high yield without adding the biotin activity-suppressing substance as mentioned above, even in a liquid nutrient medium which contains biotin at a high concentration of 10 to 1000 μ/l.

The liquid nutrient media used to cultivate the mutants according to the present invention may also contain, in addition to a carbon source, appropriate nutrients such as a nitrogen source or an inorganic ion. Useful nitrogen sources include ammonium salt, ammonia water, ammonia gas, urea, or any other compounds which are normally used as nitrogen sources for L-glutamic acid fermentation. Useful inorganic ions include phosphate, magnesium or any other alkaline or alkaline earth metal salt. In addition, trace nutrients such as thiamine may be added appropriately as necessary.

The cultivation is suitably effected under aerobic conditions. The temperature is suitably maintained at from 24° C. to 42° C. The pH is suitably maintained at from 5 to 9. The pH may be adjusted with an inorganic or organic compound or an acidic or alkaline substance such as urea, calcium carbonate or ammonia gas.

The method of recovering L-glutamic acid from the culture solution may involve an appropriate combination of known methods such as ion-exchange resin treatment or crystallization.

Having generally described this invention, a further understanding can be obtained by reference to certain specific examples which are provided herein for purposes of illustration only and are not intended to be limiting unless otherwise specified.

EXAMPLES

Obtaining Mutants

Cells of *Brevibacterium lactofermentum* ATCC 13869 were subjected to conventional mutagenetic treatment using N-methyl-N'-nitro-N-nitrosoguanidine (250 μg/ml, 30° C., 20 minutes), after which the cultivation was effected on an agar medium of the composition shown in Table 1 to form colonies.

TABLE 1

| Ingredients | Concentration |
|---|---|
| Polypeptone | 10 g/l |
| Yeast extract | 10 g/l |
| NaCl | 5 g/l |
| Acetic acid | 1 g/l |
| Agar | 20 g/l |
| pH 7.0 | |

The replica method was then used to isolate therefrom mutants incapable of growing on a medium containing L-glutamic acid as the only carbon and nitrogen source. That is, colonies were picked up which was unable to grow on a medium of the composition shown in Table 2 even after culturing at 30° C. for days, but which grew under the same conditions on the medium where sodium L-glutamate in Table 2 was substituted with 10 g/l of succinic acid and 1 ml/l of ammonia.

TABLE 2

| Ingredients | Concentration |
|---|---|
| Sodium L-glutamate | 10 g/l |
| $KH_2PO_4$ | 10 g/l |
| $MgSO_4 \cdot 7H_2O$ | 0.4 g/l |
| $FeSO_4 \cdot 7H_2O$ | 0.5 g/l |
| $MnSO_4 \cdot 4H_2O$ | 8.1 mg/l |
| Thiamine hydrochloride | 100 μg/l |
| Biotin | 300 μg/l |
| Agar | 20 g/l |
| pH 7.0 | |

Many mutants were thus obtained which have lower α-ketoglutaric acid dehydrogenase activity compared with the parent wild strain, *Brevibacterium lactofermentum* ATCC 13869. *Brevibacterium lactofermentum* AJ 12821 (FERM BP-4172) was selected as the representative strain. By the similar method, *Brevibacterium flavum* AJ 12822 (FERM BP-4173) and *Corynebacterium glutamicum* AJ 12823 (FERM BP-4174) were obtained using the wild strains, *Brevibacterium flavum* ATCC 14067 and *Corynebacterium glutamicum* ATCC 13032, as the parent strains, respectively. Cultures of *Brevibacterium lactofermentum* AJ 12821, *Brevibacterium flavum* AJ 12822, and *Corynebacterium glutamicum* AJ 12823 were deposited with the National Institute of Bioscience and Human-technology, Agency of Industrial Science and Technology, Ministry of International Trade and Industry, 1-3, Higashi 1-Chome, Tsukuba-shi, Ibaraki-ken 305, Japan under the provisions of the Budapest Treaty on Feb. 4, 1993, and may be accessed under the identification numbers FERM BP-4172, FERM BP-4173, and FERM BP-4174, respectively.

The α-ketoglutaric acid dehydrogenase activity of each of the above-stated three mutants and their parent strains was measured in the following manner. Twenty milliliters of a medium of the composition shown in Table 3 was poured into a 500 ml shaking flask, and subjected to sterilization at 115° C. for 10 minutes.

TABLE 3

| Ingredients | Concentration |
| --- | --- |
| Glucose | 50 g/l |
| (NH$_4$)$_2$SO$_4$ | 45 g/l |
| KH$_2$PO$_4$ | 1 g/l |
| MgSO$_4$.7H$_2$O | 1 g/l |
| FeSO$_4$.7H$_2$O | 10 mg/l |
| MnSO$_4$.4H$_2$O | 10 mg/l |
| Soy protein acid-hydrolyzate (as total nitrogen content) | 400 mg/l |
| Thiamine hydrochloride | 200 µg/l |
| Biotin | 300 µg/l |
| CaCO$_3$ | 50 g/l |
| pH 7.0 | |

The cells of the strain being tested were inoculated into the medium and cultured at 31.5° C. for 36 hours. The cells were harvested from the resulting culture by centrifugation and washed, after which they were suspended in 20 ml of a 0.1M TES (N-Tris (hydroxymethyl) methyl-2-aminoethane sulfonic acid)-NaOH buffer solution containing 30% glycerol. Then the cells were treated by ultrasonication, and the supernatant obtained by centrifugation thereof was subjected to gel filtration using a Sephadex G-25 column to produce a crude enzyme solution. Next, the α-ketoglutaric acid dehydrogenase activity of the crude enzyme solution was determined using the reaction solution of the composition shown in Table 4.

TABLE 4

| Ingredients | Concentration |
| --- | --- |
| TES-NaOH | 100 mM |
| Coenzyme A | 0.2 mM |
| Thiamine pyrophosphate | 0.3 mM |
| α-ketoglutaric acid | 1 mM |
| L-cysteine | 3 mM |
| MnSO$_4$.7H$_2$O | 1 mM |
| MgCl$_2$ | 5 mM |
| 3-acetylpyridine adenine dinucleotide | 1 mM |
| pH 7.7 | |

The reaction was initiated by adding 0.1 ml of the crude enzyme solution to 1.5 ml of the reaction solution, and the change in absorbance at 365 nm was traced at room temperature. A reaction solution lacking α-ketoglutaric acid was used as the control. The results are shown in Table 5.

TABLE 5

| Strains tested | α-ketoglutaric acid dehydrogenase activity (unit/mg protein) |
| --- | --- |
| *Brevibacterium lactofermentum* | |
| ATCC 13869 | 4.5 |
| AJ 12821 | 0.06 |
| *Brevibacterium flavum* | |
| ATCC 14067 | 4.8 |
| AJ 12822 | 0.32 |
| *Corynebacterium glutamicum* | |
| ATCC 13032 | 3.9 |
| AJ 12823 | 0.24 |

(One unit is defined as the amount of enzyme required to consume 1 µmol of 3-acetylpyridine adenine dinucleotide per minute in the reaction mixture).

As clearly shown here, all of the three mutants obtained by the methods described above had considerably lower α-glutaric acid dehydrogenase activities than the respective parent wild strains.

Example 1

A seed culture medium was prepared with the composition shown in Table 6, and 20 ml portions thereof were placed in 500 ml shaking flasks, and then subjected to sterilization. Each of the three mutants and their parent strains were inoculated into this medium, and the cultivation was effected using a reciprocal shaker for 15 hours while keeping the temperature at 31.5° C. This shall hereunder be referred to as the seed culture.

TABLE 6

| Ingredients | Concentration |
| --- | --- |
| Glucose | 50 g/l |
| Urea | 4 g/l |
| KH$_2$PO$_4$ | 1 g/l |
| MgSO$_4$.7H$_2$O | 0.4 g/l |
| FeSO$_4$.7H$_2$O | 10 mg/l |
| MnSO$_4$.4H$_2$O | 10 mg/l |
| Thiamine hydrochloride | 200 µg/l |
| Biotin | 30 µg/l |
| Soy protein acid-hydrolysate (as total nitrogen content) | 0.9 g/l |
| pH 7.0 | |

Next, a culture medium was separately prepared with the composition shown in Table 7, and 20 ml portions thereof were poured into 500 ml shaking flasks and then subjected to sterilization at 115° C. for 10 minutes. The concentration of biotin in this medium was 60 µg/l.

TABLE 7

| Ingredients | Concentration |
| --- | --- |
| Cane molasses (as glucose) | 60 g/l |
| KH$_2$PO$_4$ | 1 g/l |
| MgSO$_4$.7H$_2$O | 1 g/l |
| Thiamine hydrochloride | 100 µg/l |
| pH 7.0 | |

The above mentioned seed culture was inoculated into the respective medium at a proportion of about 10 volume %, and the cultivation was effected at 31.5° C. using a reciprocal shaker. A solution of urea at a concentration of 450 mg/ml was added in small amounts during the cultivation to maintain the pH of the culture solution at between 6.0 and 8.5. The fermentation was terminated at 36 hours and the amounts of L-glutamic acid accumulated in the culture solutions were measured.

As shown in Table 8, the accumulation of L-glutamic acid was very low with the wild strains due to the presence of excess biotin in the medium, while the mutants having low α-ketoglutaric acid dehydrogenase activity all produced and accumulated large amounts of L-glutamic acid.

TABLE 8

| Strains tested | Amounts of L-glutamic acid accumulated (g/l) |
| --- | --- |
| *Brevibacterium lactofermentum* | |
| ATCC 13869 | 7.5 |
| AJ 12821 | 34.0 |

TABLE 8-continued

| Strains tested | Amounts of L-glutamic acid accumulated (g/l) |
|---|---|
| *Brevibacterium flavum* | |
| ATCC 14067 | 6.1 |
| AJ 12822 | 32.1 |
| *Corynebacterium glutamicum* | |
| ATCC 13032 | 6.8 |
| AJ 12823 | 30.8 |

Example 2

A culture medium was prepared with the composition shown in Table 9, and 300 ml portions thereof were poured into 1 liter jar fermenters and then subjected to sterilization at ° C. for 10 minutes. The concentration of biotin in this medium was 150 µg/l.

TABLE 9

| Ingredients | Concentration |
|---|---|
| Cane molasses (as glucose) | 150 g/l |
| $KH_2PO_4$ | 1 g/l |
| $MgSO_4 \cdot 7H_2O$ | 1 g/l |
| Thiamine hydrochloride | 100 µg/l |
| Anti-foaming agent | 20 µg/l |
| pH 7.0 | |

The seed culture of each of the strains according to Example 1 were inoculated into the medium at a proportion of volume %, and the cultivation was effected at 31.5° C. with aeration and agitation. The pH of the culture solution was adjusted to 7.8 using ammonia gas. The fermentation was terminated at 32 hours and the amounts of L-glutamic acid accumulated in the culture solutions were measured.

As shown in Table 10, the accumulation of L-glutamic acid was very low with the wild strains due to the presence of excess biotin, while the mutants having low α-ketoglutaric acid dehydrogenase activity all produced and accumulated large amounts of L-glutamic acid.

TABLE 10

| Strains tested | Amounts of L-glutamic acid accumulated (g/l) |
|---|---|
| *Brevibacterium lactofermentum* | |
| ATCC 13869 | 18.3 |
| AJ 12821 | 78.3 |
| *Brevibacterium flavum* | |
| ATCC 14067 | 16.2 |
| AJ 12822 | 77.1 |
| *Corynebacterium glutamicum* | |
| ATCC 13032 | 14.8 |
| AJ 12823 | 77.2 |

Example 3

Culture media were prepared with the composition shown in Table 11 with biotin added at concentrations of 3, 10, 50, 300 and 1000 µg/l, and 300 ml portions thereof were poured into 1 liter jar fermenters and then subjected to sterilization at 120° C. for 10 minutes.

TABLE 11

| Ingredient | Concentration |
|---|---|
| Glucose | 100 g/l |
| $KH_2PO_4$ | 1 g/l |
| $MgSO_4 \cdot 7H_2O$ | 1 g/l |
| $FeSO_4 \cdot 7H_2O$ | 10 mg/l |
| $MnSO_4 \cdot 4H_2O$ | 10 mg/l |
| Soy protein acid-hydrolyzate (as total nitrogen content) | 0.4 g/l |
| Thiamine hydrochloride | 100 µg/l |
| Anti-foaming agent | 20 µl/l |
| pH 7.0 | |

The seed culture of each of the strains according to Example 1 were inoculated into the respective media at a proportion of 10 volume %, and the cultivation was effected at 31.5° C. with aeration and agitation. The pH of the culture solutions was adjusted to 7.8 using ammonia gas. The fermentation was terminated at 30 hours and the amounts of L-glutamic acid produced and accumulated in the culture solutions were measured.

As shown in Table 12, in the L-glutamic acid-producing culture media in which biotin was limited to a concentration of 3 µg/l, the amounts of accumulation of L-glutamic acid were about the same for both the parent wild strains and the mutants. On the other hand, in the media which contained biotin at concentrations of 10 to 1000 µg/l, the production of L-glutamic acid by the wild strains was subjected to inhibition, while the mutants having lower α-ketoglutaric acid dehydrogenase activity all produced and accumulated large amounts of L-glutamic acid.

TABLE 12

| Strains tested | Amounts of biotin added (µg/l) | Amounts of L-glutamic acid accumulated (g/l) |
|---|---|---|
| *Brevibacterium lactofermentum* ATCC 13869 | 3 | 49.2 |
| | 10 | 25.6 |
| | 50 | 15.3 |
| | 300 | 5.2 |
| | 1000 | 3.1 |
| *Brevibacterium lactofermentum* AJ 12821 | 3 | 51.3 |
| | 10 | 51.5 |
| | 50 | 52.4 |
| | 300 | 53.3 |
| | 1000 | 53.6 |
| *Brevibacterium flavum* ATCC 14067 | 3 | 46.8 |
| | 10 | 23.1 |
| | 50 | 13.1 |
| | 300 | 4.2 |
| | 1000 | 3.8 |
| *Brevibacterium flavum* AJ 12822 | 3 | 47.5 |
| | 10 | 48.1 |
| | 50 | 49.4 |
| | 300 | 50.2 |
| | 1000 | 50.6 |
| *Corynebacterium glutamicum* ATCC 13032 | 3 | 49.8 |
| | 10 | 25.7 |
| | 50 | 12.5 |
| | 300 | 5.1 |
| | 1000 | 4.6 |
| *Corynebacterium glutamicum* AJ 12823 | 3 | 48.5 |
| | 10 | 48.6 |
| | 50 | 49.5 |
| | 300 | 50.8 |
| | 1000 | 51.0 |

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method of producing L-glutamic acid by fermentation, comprising the steps of culturing a mutant of an L-glutamic acid-producing microorganism of the species *Corynebacterium glutamicum* which has an α-ketoglutaric acid dehydrogenase activity which is between 1/5 and 1/500 of that of the wild strain from which said mutant is derived, in a liquid culture medium comprising biotin at a concentration of at least 10 µg/l in the absence of a biotin activity-suppressing substance selected from the group consisting of penicillin G, penicillin F, penicillin K, penicillin O, penicillin V, penicillin X, sucrose monopalmitate, and polyoxyethylene sorbitan monopalmitate;

producing and accumulating L-glutamic acid in said culture medium in an amount greater than that produced by said wild strain; and recovering said L-glutamic acid from said culture medium;

whereby the accumulation of L-glutamic acid is not inhibited by any concentration of biotin in the culture medium within he range of 10 to 1,000 µg/l.

2. The method according to claim 1, where said concentration of biotin is of from 10 to 1000 µg/l.

3. The method according to claim 1, wherein said mutant is selected from the group consisting of

*Brevibacterium lactofermentum* (*Corynebacterium glutamicum*) AJ 12821 (FERM BP-4172);

*Brevibacterium flavum* (*Corynebacterium glutamicum*) AJ 12822 (FERM BP-4173) and

*Corynebacterium glutamicum* AJ 12823 (FERM BP-4174).

4. The method according to claim 1, wherein said α-ketoglutaric acid dehydrogenase activity of said mutant is between 1/10 and 1/100 of that of said wild strain.

5. The method according to claim 1, wherein said mutant is derived from a wild strain of *Corynebacterium glutamicum* selected from the group consisting of *Corynebacterium glutamicum* ATCC 13869; *Corynebacterium glutamicum* ATCC 14067; *Corynebacterium glutamicum* ATCC 14020; and *Corynebacterium glutamicum* ATCC 15990 and *Corynebacterium glutamicum* ATCC 13032.

6. A method of producing L-glutamic acid by fermentation, comprising the steps of culturing a mutant of an L-glutamic acid-producing microorganism of the species *Corynebacterium glutamicum*, wherein said mutant is selected from the group consisting of *Corynebacterium glutamicum* AJ 12821 (FERM BP-4172), *Corynebacterium glutamicum* AJ 12822 (FERM BP-4173) and *Corynebacterium glutamicum* AJ 12823 (FERM BP-4174), in a liquid culture medium comprising biotin at a concentration of 10 to 1000 µg/l;

producing and accumulating L-glutamic acid in the culture medium; and recovering said L-glutamic acid from said culture medium; whereby the accumulation of L-glutamic acid is not inhibited by any concentration of biotin in the culture medium within the range of 10 to 10,000 µg/l.

7. The method of claim 6, wherein said biotin activity-suppressing substance is selected from the group consisting of penicillin G, penicillin F, penicillin K, penicillin O, penicillin V, penicillin X, sucrose monopalmitate, and polyoxyethylene sorbitan monopalmitate.

* * * * *

UNITED STATES PATENT AND TRADEMARK OFFICE
CERTIFICATE OF CORRECTION

PATENT NO. : 5,492,818

DATED : February 20, 1996

INVENTOR(S) : Hidetsugu NAKAZAWA et al.

It is certified that error appears in the above-identified patent and that said Letters Patent is hereby corrected as shown below:

Column 1, line 10, "L-Glutamic" should read --L-glutamic--.

Column 3, line 38, "1000 $\mu$/l." should read --1000 $\mu$g/l.--.

Column 4, line 21, "was" should read --were--.

Column 7, line 18, "°C." should read --120°C--.

Column 7, line 34, "of volume %," should read
   --of 10 volume %,--.

Column 9, line 25, "he" should read --the--.

Signed and Sealed this

Seventeenth Day of December, 1996

Attest:

BRUCE LEHMAN

*Attesting Officer*      *Commissioner of Patents and Trademarks*